United States Patent [19]
Finburgh et al.

[11] Patent Number: 5,537,853
[45] Date of Patent: Jul. 23, 1996

[54] AIR-IN-LINE SENSING APPARATUS

[75] Inventors: Simon E. Finburgh; Matthew G. Morris, both of San Diego; Eric A. Warner, Vista, all of Calif.

[73] Assignee: IVAC Corporation, San Diego, Calif.

[21] Appl. No.: 305,466

[22] Filed: Sep. 12, 1994

[51] Int. Cl.$^6$ .................................. G01N 29/00
[52] U.S. Cl. ........................... 73/19.03; 73/19.11
[58] Field of Search ................. 73/19.03, 19.11

[56] References Cited

U.S. PATENT DOCUMENTS

| | | | |
|---|---|---|---|
| 3,171,273 | 3/1965 | Dijkema | 73/19.1 |
| 3,182,487 | 5/1965 | Graham | 73/19.1 |
| 3,225,585 | 12/1965 | Wohnoutka | 73/19.1 |
| 3,486,370 | 12/1969 | Chedeville et al. | 73/19.1 |
| 3,974,681 | 8/1976 | Namery | 73/67.5 R |
| 4,418,565 | 12/1983 | St. John | 73/19 |
| 5,394,732 | 3/1995 | Johnson et al. | 73/19.1 |

Primary Examiner—Thomas P. Noland
Assistant Examiner—Jay L. Politzer
Attorney, Agent, or Firm—Fulwider Patton Lee & Utecht

[57] ABSTRACT

An air-in-line sensing apparatus for use with a parenteral fluid administration set to detect the passage of air through a fluid conduit. The apparatus comprises a first housing having a first arcuate section mounting a first transducer adjacent the first arcuate section and a second housing having a second arcuate section mounting a second transducer adjacent the second arcuate section. One housing is independently movable relative to the other housing so that when the movable housing is moved towards the other housing, the first and second arcuate sections capture a length of administration set tubing therebetween providing secure intimate contact therewith. A signal may be generated from one of such transducers, passed through the fluid conduit and received by the other transducer to detect whether the conduit is carrying air.

41 Claims, 6 Drawing Sheets

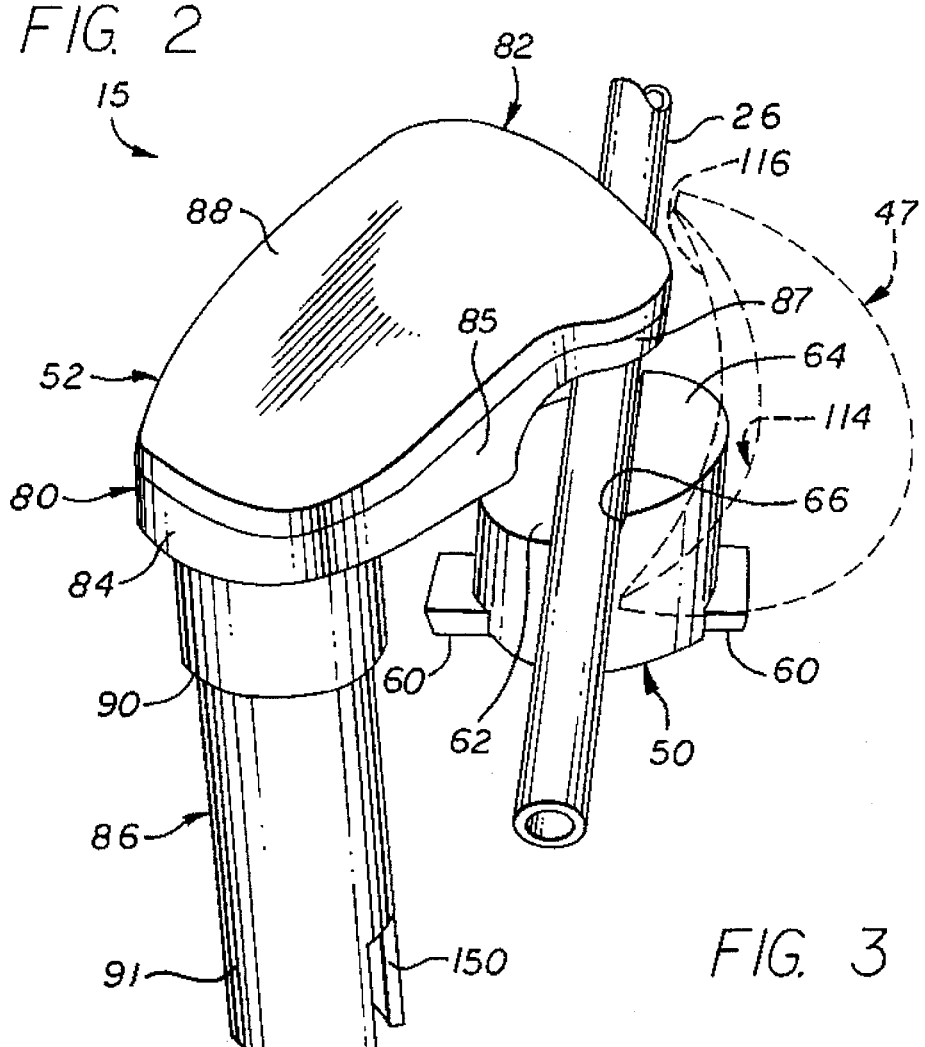
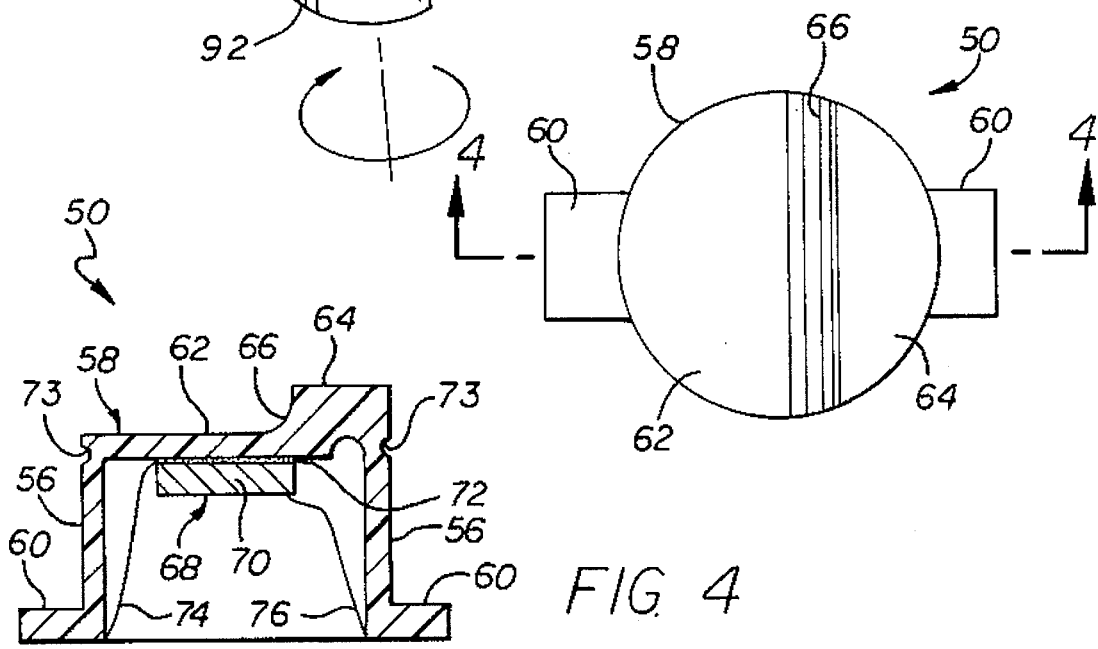

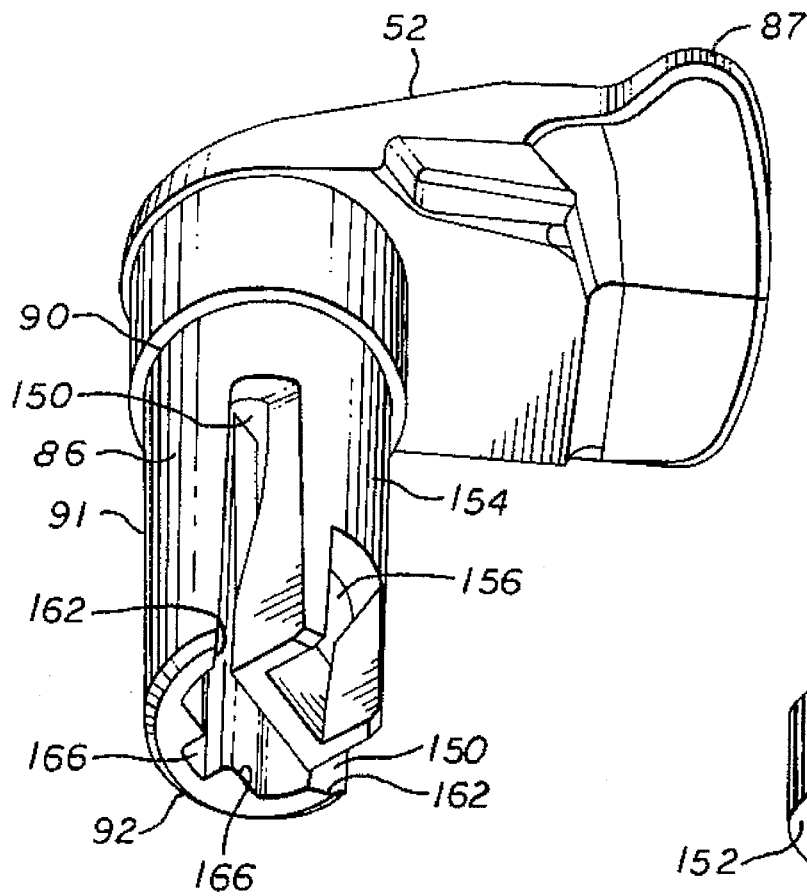
FIG. 5
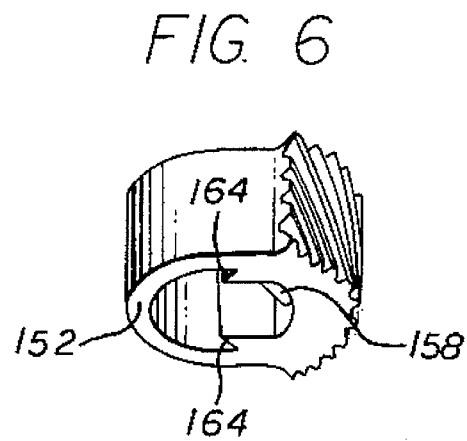
FIG. 6
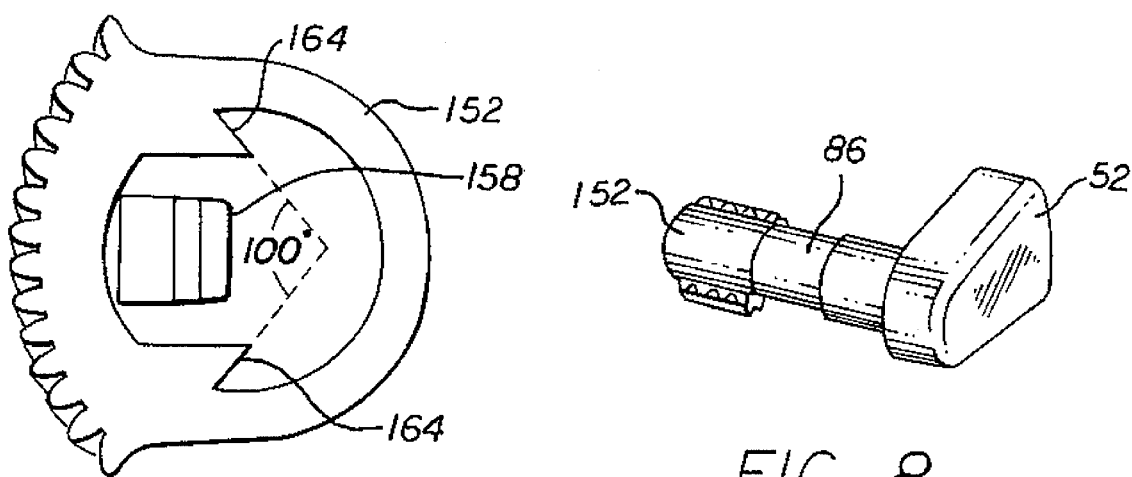
FIG. 7
FIG. 8

AIR-IN-LINE SENSING APPARATUS

BACKGROUND

The invention generally is related to monitoring the flow of fluids through a conduit, and more particularly, to detecting the presence of air in a liquid in the conduit.

In patient care facilities, the infusion of a parenteral solution into a patient is typically achieved by suspending an inverted bottle or fluid reservoir above the patient and interconnecting a fluid administration set between the reservoir and the patient. The administration set includes a conduit through which a parenteral solution flows. The free end of the tubing is connected to a cannula that is inserted into a blood vessel of the patient.

An infusion pumping mechanism may be used in conjunction with the fluid administration set to facilitate fluid infusion to the patient at a prescribed and regulated flow rate. The pumping mechanism may be engaged along an intermediate length of administration set tubing and actuated to pump the parenteral fluid through such tubing at the prescribed rate.

A peristaltic pump is one such type of infusion pumping mechanism that uses sequential occlusion of the administration set tubing to move the fluid through the tubing and to the patient. Linear type peristaltic pumps include a plurality of adjacent reciprocating pumping fingers, the fingers being sequentially urged against a length of fluid administration set tubing to occlude adjacent segments thereof in wave-like action forcing fluid through the tubing.

In fluid administration systems, it is important that introduction of air into a patient's blood vessel be avoided. Should an excessive quantity of air be introduced into a blood vessel, a condition known as air embolism may result whereby an air bubble may form in the blood vessel causing a blood flow obstruction. Consequently, it is desirable to include a monitoring device to monitor the fluid flowing in the administration set tubing so that an attendant may be notified if air above a certain quantity has been detected in the tubing. Once air has been detected, measures may be taken to prevent air from being introduced into a patient's blood vessel.

Devices for detecting the presence of air in a fluid conduit have been developed, such devices including in one case, an acoustic means to transmit a signal through the fluid conduit to an acoustic receiver that then transmits the received signal to a processor. The processor analyzes the received signal to determine whether air is present in the fluid conduit.

In one prior art air detection device, a U-shaped base forms a cavity between the branches of the U. A first transducer, an ultrasonic transmitter, is mounted on one branch of the U and a second transducer, an ultrasonic receiver, is mounted to the opposing branch of the U, each having an ultrasonic lens protruding into the cavity. In this device, the transmitter and receiver are semi-circularly convex and are spaced apart to receive a flexible fluid conduit between them and compress the side walls of the fluid conduit to obtain good contact. Good contact between the transducers and the object under test is essential to avoid any leakage of the transmitter signal through the air around the object rather than through the object. Such leakage would be considered to be the detection of air by the processor and a false alarm may result. Thus, if a substantial surface area of each of the respective transducers is exposed to outside air, the signal-to-noise ratio will decrease and may result in false or inaccurate readings. Therefore, to minimize such signal-to-noise interference and improve signal strength, it is desirable to improve the surface contact area between the transducer and the surface of the fluid conduit, while in turn preventing the introduction of contaminants between them.

Another prior art device has a hollow U-shaped body, the respective branches of the U each mounting a concave ultrasonic transducer aligned in diametrically opposed positions, the transducers configured for receipt of a length of fluid conduit. When the fluid conduit is installed between the concave transducers, a length of fluid conduit is manually inwardly compressed by the user and manipulated between the concave transducers and the end of the U-shaped body. A concave cover is closed over the fluid conduit to slightly compress and encircle the conduit. Although this device has proven effective in use, it has been found desirous to have such a device constructed so that when the conduit is installed, such conduit is correctly aligned between the pair of transducers automatically without any undue effort.

Hence, those skilled in the art have recognized the need for a monitoring device for detecting the presence of air in a fluid conduit that provides a fluid conduit capturing feature for automatically aligning the fluid conduit adjacent sensing transducers. Furthermore, such device should provide improved surface contact between the transducer and the fluid conduit for increased monitoring accuracy. In addition, a device of this nature should be cost effective and easy to manufacture. The present invention fulfills these needs.

SUMMARY OF THE INVENTION

The present invention is directed to an apparatus for sensing the presence of air in a liquid in a fluid conduit, the apparatus including a conduit capturing feature for automatically aligning the conduit in the apparatus, while providing intimate surface contact between the conduit and a sensing device.

Briefly, the apparatus includes a first housing having a first arcuate section and a second housing having a second arcuate section, the respective arcuate sections adapted to receive the fluid conduit therebetween. The first housing includes a first transducer adjacent the first arcuate section and the second housing includes a second transducer adjacent the second arcuate section whereby one of such transducers transmits a signal across the conduit and fluid contained therein and the other transducer receives such signal. The receiving transducer converts the received acoustic signal into an electrical signal whereby a processor determines whether the fluid conduit is carrying air or liquid. The first and second housings are spaced a predetermined distance apart and are independently movable with respect to each other.

In a more particular aspect of the invention, one of the housings may be rotatably moved to an open conduit receiving position and the conduit placed adjacent thereto. Thereafter, the housing may be rotated relative to the other housing during which the respective housings capture the conduit between themselves to align the fluid conduit substantially in a parallel relationship between the first and second arcuate sections.

In another aspect of the invention, the signal that passes through the conduit and fluid contained therein is an ultrasonic signal. In a further aspect of the invention, the first arcuate section is aligned substantially parallel to the second arcuate section, the conduit being slightly compressed therebetween.

In another aspect of the invention, the respective arcuate sections of the first and second housings are formed as concave arcs of approximately ninety degrees. In a further aspect of the invention at least one of such arcuate sections further comprises an arcuate tapered flare to assist in capturing the fluid conduit.

Other features and advantages of the invention will become apparent from the following detailed description taken in conjunction with the accompanying drawings, which illustrate by way of example, the features and advantages of the invention.

BRIEF DESCRIPTION OF THE DRAWINGS

FIG. 2 is an enlarged perspective view of the air-in-line sensing apparatus shown in FIG. 1 depicting a fluid administration conduit in a receiving position between first and second housings of the air-in-line sensing apparatus in accordance with the invention;

FIG. 3 is an enlarged top view of the first housing of the air-in-line sensing apparatus shown in FIG. 2;

FIG. 4 is a cross-sectional side view of the first housing of the air-in-line sensing apparatus taken along line 4—4 of FIG. 3;

FIG. 5 is a perspective view of a second housing and its shaft having a snap fit feature for receiving a helical gear segment;

FIG. 6 is a perspective view of a helical gear segment usable with the shaft of the second housing of FIG. 5 and usable with the snap fit feature of that shaft;

FIG. 7 is a top view of the helical gear segment of FIG. 6 more clearly showing the tongue used in the snap fit feature of FIG. 5;

FIG. 8 is an assembled view of the housing and shaft of FIG. 5 with the helical gear segment of FIG. 6;

DETAILED DESCRIPTION OF THE PREFERRED EMBODIMENTS

Figure 1:
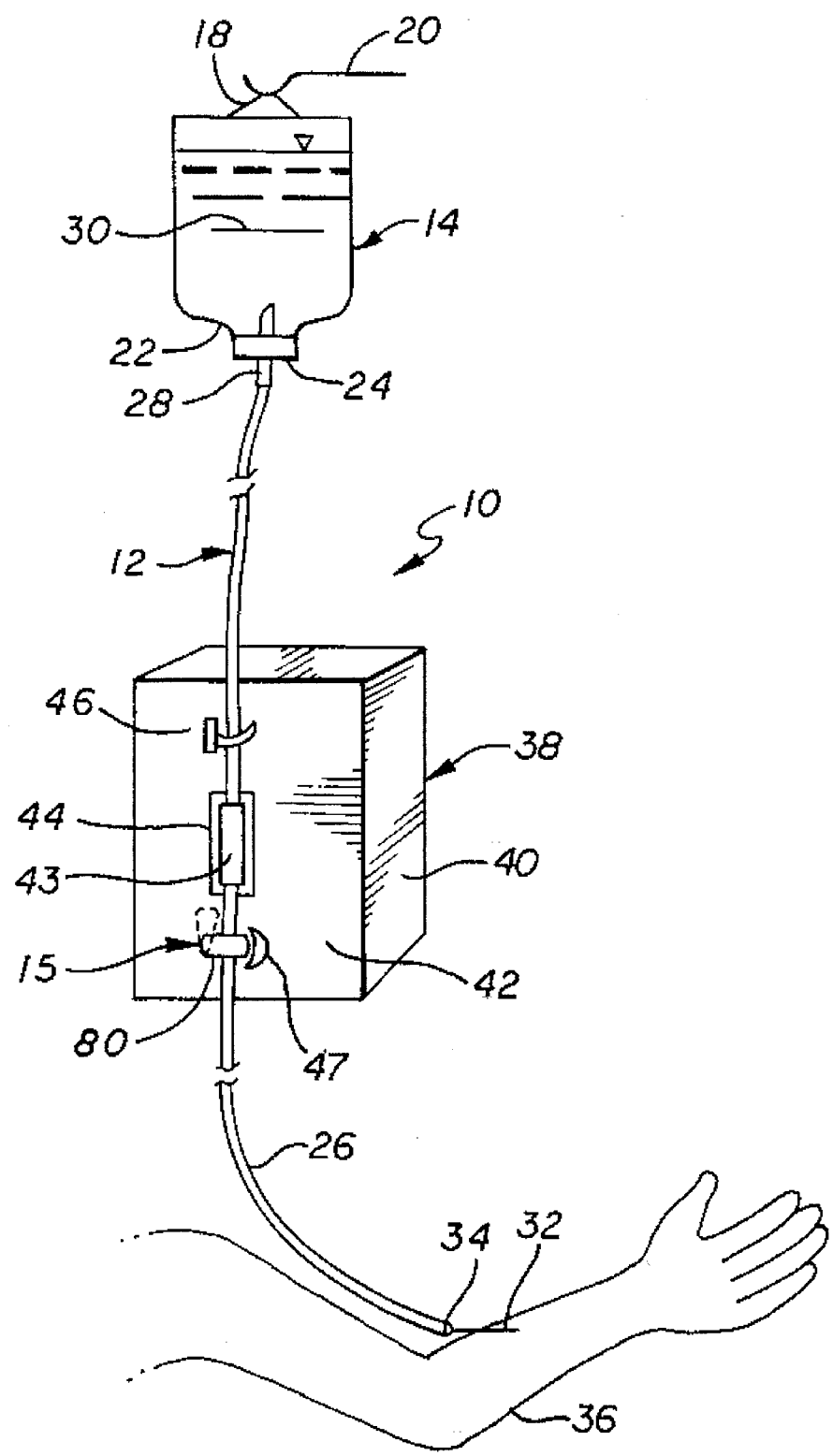
FIG. 1 is an elevational view of a parenteral fluid delivery system showing an inverted parenteral fluid container connected to a parenteral fluid administration set, the set being connected to an infusion pumping system including an air-in-line sensing apparatus of the invention.

In the following description, like reference numerals will be used to refer to like or corresponding elements in the different figures of the drawings. Referring now to the drawings and particularly to FIG. 1, there is shown a parenteral fluid intravenous infusion system 10 including an administration set 12 in fluid communication with an inverted parenteral fluid container 14. The infusion system includes an air-in-line sensing apparatus 15 in accordance with principles of the present invention.

As shown in FIG. 1, the inverted parenteral fluid container 14 has a bottle shaped reservoir 14 including a hook mechanism 18 on the bottom end thereof connected to support rod 20 of a stand (not shown). The bottle reservoir has a reduced diameter neck 22 having a stopper 24 disposed therein.

The administration set 12 comprises a fluid conduit, such as a length of flexible and compressible polyvinyl chloride ("PVC") tubing 26, the top end thereof connected to a vented penetrant 28. The vented penetrant has a fluid bore therethrough, the top end thereof converging to a sharpened point. As shown in FIG. 1, the vented penetrant 28 has been inserted through the stopper 24 of the parenteral fluid container 14 so that the top end thereof is placed in fluid communication with parenteral fluid 30 contained in the reservoir 14.

The free end of the administration set tubing 26 is connected to an infusion cannula 32, the cannula attached to the free end of the tubing at a needle hub 34. The distal end of the infusion cannula is introduced into a blood vessel of a patient 36 for administration of the parenteral fluid to the patient.

A fluid flow control device, such as a volumetric infusion pump 38, may be utilized to regulate the flow rate of parenteral fluid through the administration set. One such type of infusion pump may be, for instance, a linear peristaltic pump 38, and is shown for purposes of illustration. Linear type peristaltic pumps typically include a pump housing 40 having a front panel 42 that includes controls, displays (not shown) and a mounting system for the fluid conduit 26. In the case shown in FIG. 1, the administration set 12 includes a dedicated pumping segment 43 (shown in dashed lines) that is engaged by the plurality of peristaltic pumping fingers 44. The peristaltic pump, when actuated, causes the pumping fingers to sequentially occlude adjacent segments of the pumping segment in a wave-like motion to force fluid through the tubing and to the patient. A tubing locking mechanism 46 is vertically aligned above the pumping fingers 44.

Figure 11:
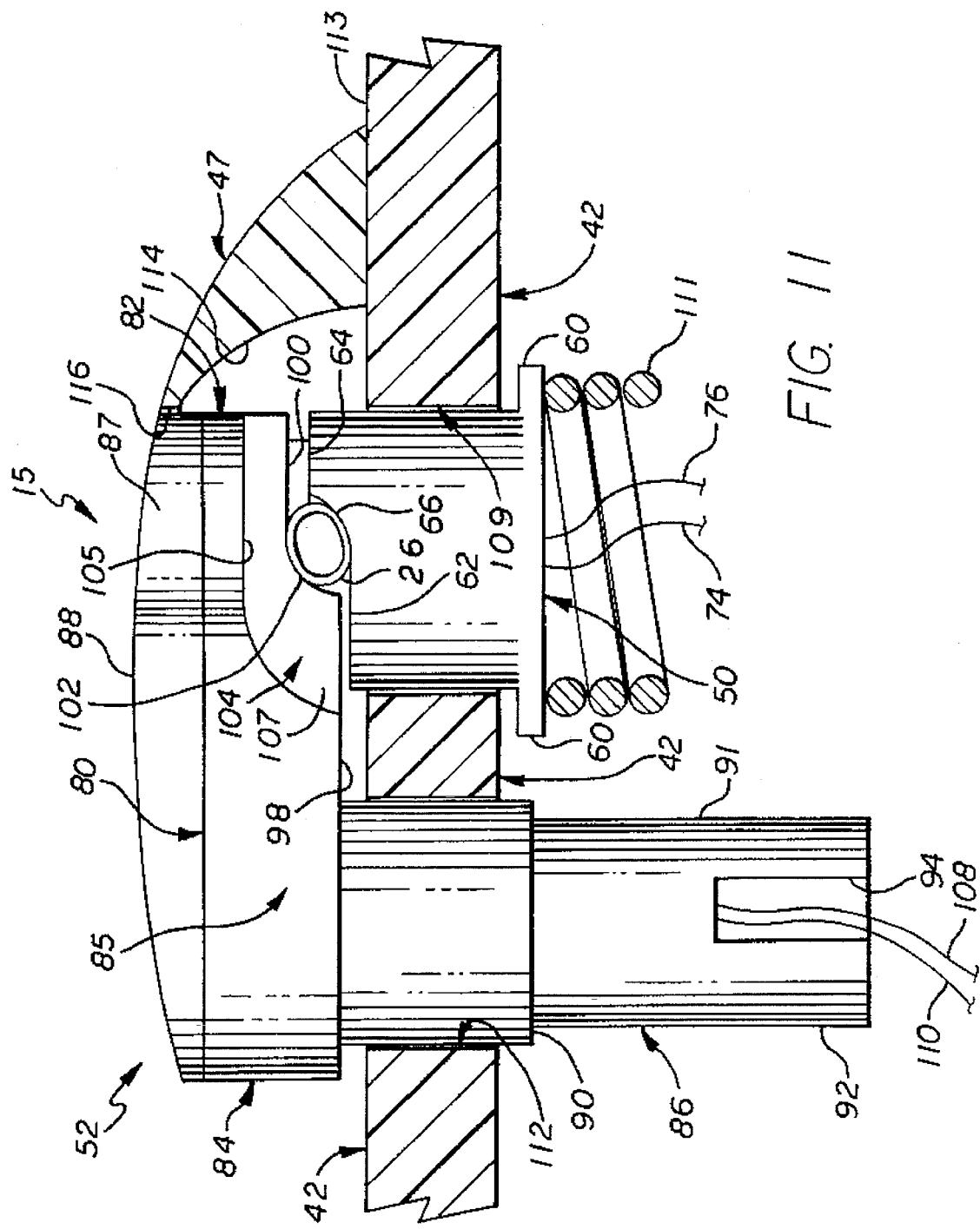
FIG. 11 is a side view of the first and second housings of the air-in-line sensing apparatus of FIG. 2, illustrating such housing in an operatively closed position engaging the fluid conduit therebetween.

The air-in-line sensing apparatus 15 of the invention is disposed downstream from the pumping fingers 44 and is mounted to the front panel 42 of the pump housing 40. The pumping segment 43 of the administration set tubing 26 is operatively engaged with the peristaltic mechanism 44 between the tubing locking mechanism 46 and the air-in-line sensing apparatus 15. As shown in FIG. 11, the air-in-line sensing apparatus is in its operative position wherein the tubing 26 is aligned properly in the sensing apparatus.

A generally half-dome shaped member 47 is disposed adjacent the air-in-line sensing transducers to assist in guiding the tubing into the correct position between the transducers.

Referring now to FIG. 2, the air-in-line sensing apparatus 15 in accordance with the invention will be described in detail. In general, the air-in-line sensing apparatus includes first and second housings, generally indicated at 50 and 52 respectively. The housings are formed independently of one another and the second housing is independently movable relative to the first housing.

With particular reference to FIGS. 3 and 4, the first housing 50 is generally formed as a hollow open cylinder having vertically extending side walls 56 extending up to a top end 58. The bottom end of the open cylinder has a pair of outwardly extending oppositely projecting mounting ears 60. The upper surface of the upper wall of the first housing is formed with a generally smooth horizontal planar upper surface 62 transitioning to a raised ridge 64 also having a generally horizontal planar top surface, the transition being formed transverse to the long axis of the cylinder and slightly off the axial centerline thereof to define first arcuate portion 66. The first arcuate portion may be generally characterized as a smooth concave fillet formed between a ninety degree step transition from the smooth planar surface 62 to the raised ridge 64. In the preferred embodiment, the first arcuate portion 66 is formed, on end, as a ninety degree radiused circular sector.

With particular reference to FIG. 4, a first transducer 68 is fixedly secured to the bottom surface of top 58 of the first housing 50. In the preferred embodiment, the transducer is an ultrasonic transducer of a type well known in the art. In particular the transducer is in the form of a rectangle, sized to conform to features on the inside of the cylindrical side walls 56 of first housing. The transducer may include a piezoelectric crystal 70 bonded to the bottom surface of the upper surface by an epoxy 72. The epoxy thickness is carefully controlled to ensure acoustic energy transfer from the piezoelectric crystal to the housing. A pair of electrical leads 74 and 76 are attached to the opposite sides of the piezoelectric crystal and are directed out of the cylinder for connection to electronic equipment used to analyze the acoustical signals received by the piezoelectric crystal. In this embodiment, the transducer of the first housing 50 receives the ultrasonic signal. However, the opposite arrangement is also possible; i.e., where the transducer of the second housing 52 receives the ultrasonic signal transmitted by the transducer of the first housing.

In the preferred embodiment, the first housing of the air-in-line sensing apparatus is composed of a polymeric material, such as ABS, and is formed as one piece by an injection molding process or the like to provide a single unitary body. Additionally, a recess 73 is formed around the first housing to receive a seal (not shown) when mounted to the front panel. The seal will prevent fluids from entering into the interior of the pump.

Referring back to FIG. 2, the second housing 52 is formed generally with a contoured upper portion 80 having forward, rearward and front ends, 82, 84 and 85 respectively, and a hollow shaft 86 projecting downward from the rearward end 84 of the upper portion. The front forward end 82 of the second housing further includes an outwardly projecting hook portion 87. The upper portion 80 is generally hollow and includes a complementary formed cap 88 to enclose electrical components, described below. The shaft is generally an elongated hollow cylinder having a reduced-in-diameter step 90 extending downward therefrom to the bottom end 92 of the shaft to define a reduced-in-diameter cylindrical portion 91.

In one embodiment, the shaft 86 has a helical gear segment 152 mounted to it to for effecting rotation of the second housing 52 to move the housing 52 into and out of operational position over the first housing 50. Referring now to FIGS. 5 through 8, the shaft 86 includes a pair of slots 150 spaced apart arcuately. These slots are used to provide surfaces to engage the helical gear segment 152 to receive rotational forces received by that gear segment to the shaft. As a result of forming the slots along a length of the shaft, a snap fit member 154 lying between the slots remains as part of the shaft and is flexible. The snap fit member 154 includes an aperture 156 in which a rigid tongue 158 of the helical gear segment is received. When slid onto the shaft from its distal end 92, the tongue 158 of the helical gear 152 causes the bendable snap fit member 154 to bend inward until the tongue reaches the aperture 156. The tongue 158 then enters the aperture and the snap fit member 154 flexes back to its normal position thus locking the tongue of the helical gear in the aperture and locking the helical gear segment 152 to the shaft 86. This structure enables quick connect and disconnect of the helical gear segment with the shaft. To disconnect, the user manually bends the snap fit member 154 inward until the tongue is free of the edge of the aperture and then slides the helical gear segment off the shaft.

The slots 150 in the shaft 86 are shaped to form angular wedges 162 on the shaft. These angular wedges mate with complementary angular wedges 164 on the helical gear segment 152 when the two are assembled together as shown in FIG. 8. The wedges 162 and the portion of the shaft connecting them are the load-bearing portions of the shaft that receive the forces transmitted by the helical gear segment 152. Because the aperture and the tongue are located opposite the load bearing portion, the snap fit of the tongue into the aperture will not become disengaged by itself as a result of the transmission of rotational force through the helical gear segment 152. A manual bending of the flexible portion 154 inward will be required to separate the tongue 158 from the aperture 156.

The configuration of the load-bearing portion of the shaft appears as a "C" and in this embodiment extends over an angle greater than one-hundred and eighty degrees. As shown in FIG. 7, the wedges have an included angle of 100 degrees and are angled in relation to radii of the opening of the gear 152 for receiving the shaft. The combination of the angular wedges 162 and 164, the C shape and the extent of the load-bearing angle decouples the rotational forces from the snap fit feature so that the snap fit of the helical gear segment with the shaft remains intact over all design loads.

Also shown in FIG. 5 is a channel 166 formed in the material of the shaft 86 for receiving the electrical wires (not shown) of the transducer in the second housing 52. This channel is formed in the end 92 of the shaft because the snap fit member 154 may be bent inward far enough to contact the inside surface of the load-bearing member 166. Thus the electrical wires are removed from possible contact with the member 154 during assembly and any disassembly that may occur.

The cap 88 is complementarily contoured for mating the bottom peripheral edge thereof to the upper portion 80 of the second housing 52. As illustrated, the top surface of the cap is slightly domed.

Figure 9:
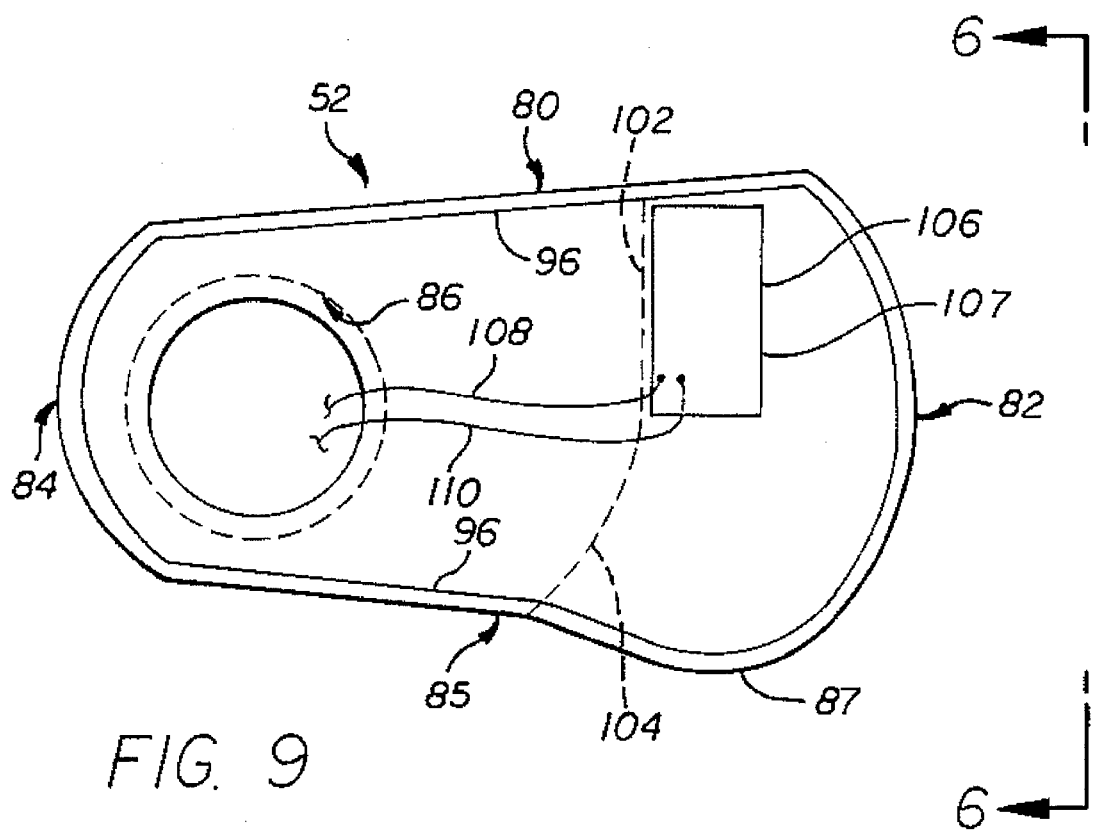
FIG. 9 is an enlarged bottom view of the second housing of the air-in-line sensing apparatus shown in FIG. 2.
Figure 10:
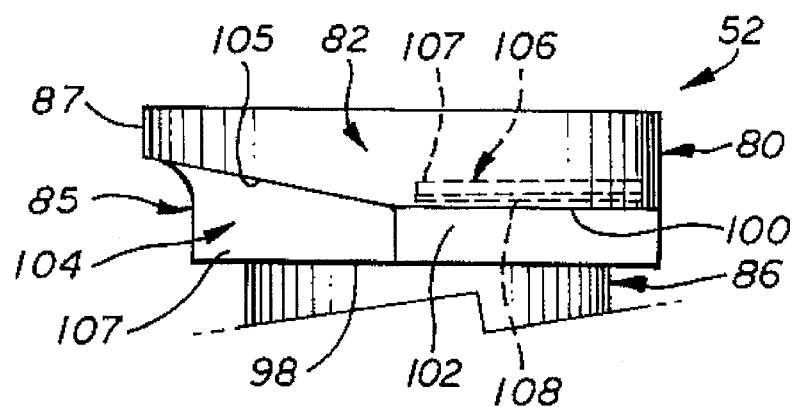
FIG. 10 is a side view of the second housing of the air-in-line sensing apparatus shown in FIG. 9.

Referring particularly to FIGS. 9 and 10, the second housing 52 is described in more detail. For purposes of illustration, the cap 88 of the second housing has been removed and is not shown. The upper portion 80 of the second housing may be generally considered rectangular in shape having a shallow upstanding side wall 96 around the periphery thereof. The shaft 86 is formed at the rearward end 84 extending downwardly from upper portion 80 so that the cylindrical hollow of the shaft is accessible from the upper portion.

Referring to FIGS. 10 and 11, the bottom surface 98 of the upper portion 80 of the second housing 52 has a generally smooth planar horizontal section transitioning to a raised smooth horizontal planar surface section or shelf 100 at the forward end 82 of the upper portion. The transition is formed transverse to the longitudinal extent of the upper portion to define a second arcuate portion 102. The second arcuate portion 102 may be generally characterized as a smooth concave fillet formed between a ninety degree step transition from the bottom planar surface 98 to the planar shelf 100. In the preferred embodiment, the second arcuate portion is formed, on end, as a ninety degree radiused circular sector. The second arcuate portion 102 is formed with an arcuate tapered flare 104 that tapers and curves in two dimensions, rearwardly and upwardly to the front end 85 of the upper portion 80 of the second housing 52 beneath the projecting hook 87.

In the preferred embodiment, the second housing 52 of the air-in-line sensing apparatus comprises a polymeric material, such as ABS, and is formed as one piece by an injection molding process or the like to provide a unitary body.

With reference to FIGS. 9 and 10, a second transducer 106 is located within the upper portion 80 of the second housing 52 and is positioned atop the planar shelf 100 at the forward end 82 of the second housing. In the preferred embodiment, the second transducer is an ultrasonic transducer of a type well known in the art. In particular, the second transducer is in the form of a flat thin rectangular plate, the longitudinal length thereof positioned in parallel alignment generally adjacent and above the second arcuate portion 102 of the second housing.

The second transducer may include a piezoelectric crystal 106 bonded to the surface above the planar shelf 100 by an epoxy 107. The epoxy and polymer that it is bonded to may serve as an acoustical lens to focus acoustic energy from the bottom surface of the piezoelectric crystal to the outside surface of the housing. The pair of electrical leads 108 and 110 are affixed to the respective upper and lower faces of the piezoelectric crystal 107, the free ends thereof being received through the hollow of the shaft 86 and connected to electrical equipment for exciting the piezoelectric crystal to transmit acoustical energy.

The air-in-line sensing apparatus 15 may be used in conjunction with a fluid infusion pumping system, and is shown for purposes of illustration mounted to a peristaltic type pumping system 38 (FIG. 1). The first and second housings, 50 and 52, of the air-in-line sensing apparatus, are mounted to the front panel 42 of the pump housing 40. In its unactuated tubing receiving position, the upper portion 80 of the second housing 52 of the air-in-line sensing apparatus 15 is oriented in a vertical upwardly predisposed position. When the air-in-line sensing device is in its operatively closed position, the second housing is rotated, from its vertical upward position, approximately one-quarter turn in a clockwise direction to capture and compress the administration set tubing 12 between the respective first arcuate portion 66 of the first housing 50 and second arcuate portion 102 of the second housing 52 as illustrated in FIG. 11.

With particular reference to FIG. 11, the front panel 42 is formed with a first bore 109 therethrough for slidable receipt of the cylindrical first housing 50 from the back side, the mounting tabs or ears 60 biased by a compression spring 111 to abut the back surface of the front panel. Due to the compressive force of spring 111, the first housing 50 is biased toward the second housing 52. However, the presence of the tubing 12 typically results in the first housing 50 being forced somewhat into the front panel as shown in FIG. 11. With no tubing in place, the first housing 50 would be "bottomed out" against the front panel due to the force of the compression spring 111. That is, the mounting tabs 60 would make contact with the back of the front panel to stop the first housing 50 from being pressed through the front panel by the spring 111.

Thus, tubing 26, positioned between first arcuate section 66 and second arcuate section 102, is slightly compressed, which ensures that both transducers are covered by the compressed tubing and thus will sense no external air to cause false or inaccurate readings. Furthermore, it has been noted that the tubing has a tendency to deform under slight compression over extended periods of time. The spring biasing of the first housing relative to the second housing ensures that the respective arcuate sections 66 and 102 and respective planar surfaces 62 and 100 maintain intimate contact with the tubing even if such tubing has deformed.

A second bore 112 is formed through the front panel for slidable receipt of the shaft 86 of the second housing 52. The shaft is slidably received within the second bore from the front surface of the front panel so that the bottom end 92 of the shaft extends into the pump housing. The shaft is rotatably mounted therein by means well known in the art, for instance by a spring clip or the like.

Figure 12:
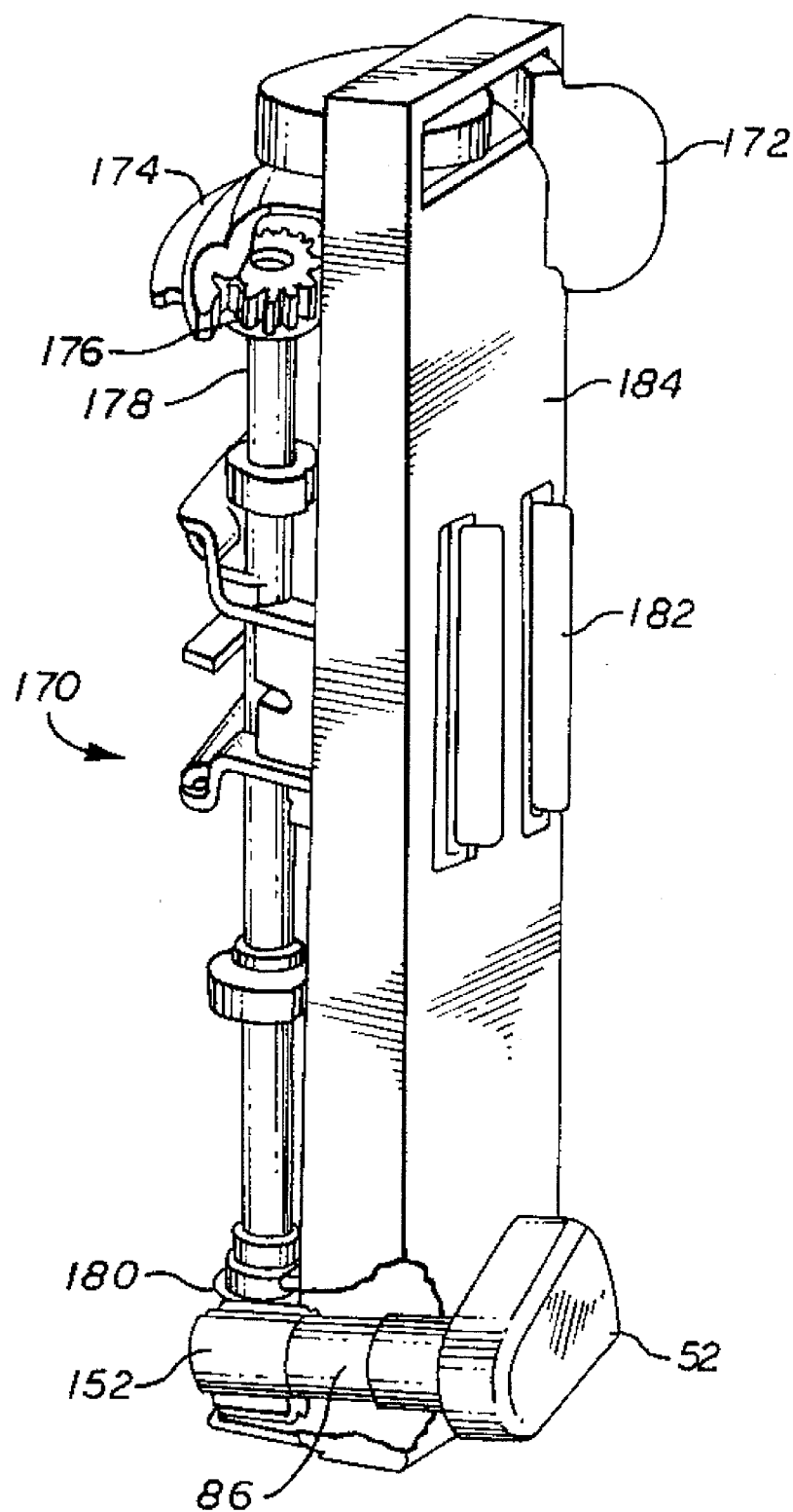
FIG. 12 is a cutaway view of a mechanism usable with the second housing to control the position of the second housing.

Referring now to FIG. 12, a rotational mechanism 170 for rotating the second housing 52 into and out of operational position is illustrated. A latch lever 172 is provided for manually causing the rotation. The distal end of the latch lever is connected via ring gear 174 with another gear 176 mounted firmly to the end of a driving shaft 178. Movement of the latch lever 172 thus causes rotation of the driving shaft 178. At the opposite end of the driving shaft 178 is a second gear 180. The helical gear segment 152 is coupled to this second gear and transmits the rotation movement of the second gear 180 to the shaft 86 of the second housing 52. Thus movement of the latch lever 172 causes rotation of the second gear which in turn causes rotation of the second housing 52.

The driving shaft 178 is also shown connected to a clamp system 182 that may be used to firmly grasp a pumping segment (not shown) to the front panel 184. Rotation of the latch lever 172 will therefore cause both the clamp to engage a pumping segment as well as bring the second housing 52 into operational position over the pumping segment to sense air in the line.

It is to be appreciated that in the alternative, the second housing 52 of the air-in-line sensing apparatus 15 may be rotatably actuated by the user by simply rotating the second housing relative to the first housing 52 manually, whereby a releasable locking means, well known to those skilled in the art, may be incorporated therewith to lock the second housing relative to the first housing.

With reference to FIGS. 2 and 11, the guide member 47 is mounted to the front surface of the front panel 42 of the pump housing and is positioned so that when the second housing is in its operative position, the forward end 82 of the second housing is positioned in a closely spaced relationship adjacent the guide member 47. As shown in dashed lines in FIG. 2, the guide member is generally formed as a solid half dome having an inwardly depressed quarter-spherical surface 114, the upper outer peripheral edge 116 of the half-dome being inwardly curved.

With reference to FIGS. 1, 2 and 11, the installation of the administration set tubing 26 into the air-in-line sensing apparatus 15, as well as the operation thereof are described in detail. To install the tubing in the infusion pumping mechanism, the second housing 52 of the air-in-line sensing apparatus 15 would be in its vertical (upright) open tubing-receiving position, shown in dashed lines in FIG. 1. When in this position, the pumping segment 43 of the administration set tubing 26 is placed into position over the pumping fingers 44 of the pumping mechanism and a segment of the tubing is disposed within an aperture in the tubing locking mechanism 46. With reference to FIG. 2, the flexible administration set tubing 26 is placed over the planar surface 62 of the first housing 50 generally adjacent the first arcuate portion 66 thereof.

The tubing 26 may not be longitudinally straight, as shown, because tubing is typically coiled in packaging for shipping. Therefore, when the tubing is uncoiled, there may be bends in the tubing when installed in the air-in-line sensing apparatus 15 which may cause segments of the tubing to be spaced apart from the upper surface 62 or from the first arcuate portion 66 of the first housing.

To operatively engage the tubing 26 within the air-in-line sensing apparatus 15, the second housing 52 is rotated approximately one quarter turn in a clockwise direction from a vertically upright position to a generally horizontal position. If the tubing is bent in a direction toward the guide member 47, the guide member confronts the tubing to hold the tubing to limit it from moving farther away from the first housing as the second housing is rotated into position. The guide member 47 also assists in bringing the tubing into alignment between the first and second housings. If the tubing is bent outwardly from the front panel 42, the projecting hook 87 of the second housing will hook and urge the tubing downward into alignment between the first and second housings as the second housing is rotated. Furthermore, if the tubing is bent in a direction toward the second housing, such second housing confronts the tubing to maintain the tubing in such position so that the second housing, when rotated, captures the tubing between the first and second housings, as described in detail below.

As the second housing 52 is rotated, the upper slanted surface 105 of arcuate tapered flare 104 slidably engages the tubing 26 to urge such tubing downward against the upper surface 62 of the first housing 50. In addition, as the second housing is rotated, the downwardly extending surface 107 of the arcuate tapered flare 104 slidably engages the side wall of the tubing to urge such tubing horizontally toward the first arcuate portion 66 of the first housing. As the second housing is further rotated, the tubing 12 is urged into parallel alignment between the first and second arcuate portions 66, 102 as the second housing is rotated to its horizontal closed position, whereby the first and second arcuate portions come into parallel alignment with each other providing, in essence, an automatic tube-loading feature.

As the second housing 52 is rotated, arcuate tapered flare 104 slides along the outer surface of the conduit to sweep and clean debris and fluid therefrom which may have collected on the surface thereof. The clean surface of the tubing allows for more accurate acoustical signal transmission through the tubing 26 and fluid carried therein.

Once the second housing 52 is fully rotated to its operative or closed horizontal position to capture the tubing between the housings, the arcuate portions, 66 and 102 slightly compress the walls of the tubing 26 inwardly so that intimate positive contact is insured between the respective arcuate portions of the housings and the tubing while minimizing tubing distortion. It is important that such intimate contact be provided, because if air is trapped between the tubing and the arcuate portions, inaccurate or false readings may be incurred due to the transducers effectively sensing such air and not being able to distinguish air outside the tubing from air in the fluid carried in the tubing. Such contact improves ultrasonic signal strength and therefore improves the signal-to-noise ratio of the transducers. In addition, once the tubing has been captured between the housing 50 and 52, the parallel alignment and the selected spaced-apart configuration of the arcuate portions 66 and 102, as well as the spring loading provide such intimate contact over extended durations.

The spring loading of one of the housings provides compensation for reduced tubing size in the case where the tubing is pulled axially. In the case where a significant pulling force is applied to the tubing downstream and its walls are made thinner and its diameter is caused to decrease as a result of stretching, the spring 111 will automatically cause the first housing 50 to continue to make good contact with the reduced-diameter tubing.

It is to be appreciated that an air-in-line sensing apparatus constructed in accordance with the invention may be incorporated in other types of fluid administration sets and other types of fluid infusion devices. For example, the apparatus may be used in the case where a syringe pump provides the force to move the fluid through the conduit.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. An apparatus for detecting a gas in a liquid contained in a conduit, comprising:

a first housing having a first transducer for transmitting a signal across said conduit;

a second housing having a second transducer for receiving said signal;

wherein said first housing and said second housing are spaced a distance apart and one housing is independently rotatable in relation to the other housing; and means for simultaneously capturing and aligning said conduit between said first and second transducers whereby said first transducer transmits said signal across said conduit and is received by said second transducer which converts said signal into an electrical signal which is processed and which will establish whether said fluid-carrying conduit is carrying a gas.

2. The apparatus according to claim 1, wherein said means for capturing and aligning said conduit comprises:

said first housing further including a first arcuate section which is in contact with a first arcuate section of said conduit; and said second housing further including a second arcuate section which is in contact with a second arcuate section of said conduit.

3. The apparatus according to claim 1 wherein said rotatable housing includes a shaft having a gear mounted at the end of the shaft responsive to rotation force for causing rotation of the rotatable housing.

4. The apparatus according to claim 3 wherein:

the shaft includes a snap fit member for receiving the gear and engaging the gear to retain the gear in a predetermined position on the shaft; and the snap fit feature is located opposite a load-bearing portion of the shaft.

5. The apparatus according to claim 1 wherein one of said housings is spring loaded toward the other housing to compress said conduit when said conduit has been captured and aligned between said first and second housings.

6. The apparatus according to claim 1 wherein said signal transmitted between said first and second transducers is an ultrasonic signal which passes through said conduit.

7. The apparatus of claim 1 wherein said means for capturing and aligning comprises a hook-shaped portion formed on the rotatable housing, the hook-shaped portion configured to engage the conduit and move the conduit to a position between the first and second housings during rotation of said one housing towards the other housing thereby capturing and aligning the conduit.

8. The apparatus of claim 1 wherein said means for capturing and aligning comprises an arcuate tapered flare formed on the rotatable housing, said flare configured to engage the conduit and to wipe the exterior of the conduit during rotation of said one housing towards the other housing to thereby clean the conduit of matter located on its exterior.

9. The apparatus of claim 1 wherein said means for capturing and aligning comprises a guide member located adjacent one of said housings to contain the conduit within a predetermined range of the rotatable housing.

10. The apparatus of claim 9 wherein said guide member has approximately a half-dome shape and extends to a height approximately equal to the height of the rotatable housing.

11. An apparatus for detecting a gas in a conduit, comprising:

a first housing having a first arcuate section which is in contact with a first arcuate section of said conduit;

a second housing having a second arcuate section which is in contact with a second arcuate section of said conduit;

wherein said first housing and said second housing are spaced a distance apart and one of said housings is independently rotatable in relation to the other of said housings;

a first transducer associated with said first housing for transmitting a signal across said conduit;

a second transducer associated with said second housing for receiving said signal, whereby said signal travels across said conduit and is received by said second transducer which converts said signal into an electrical signal which is processed and which will establish whether said fluid-carrying conduit is carrying the gas.

12. The apparatus according to claim 11 wherein said conduit is compressed between said first housing and said second housing.

13. The apparatus according to claim 11 wherein said first arcuate section is aligned substantially parallel to said second arcuate section and said conduit is compressed therebetween.

14. The apparatus according to claim 11 wherein said second arcuate section further comprises an arcuate tapered flare to slidably engage said conduit.

15. The apparatus according to claim 11 wherein said first arcuate section of said first housing comprises an arc of approximately 90 degrees.

16. The apparatus according to claim 15, wherein said second arcuate section of said second housing comprises an arc of approximately 90 degrees.

17. The apparatus according to claim 11, wherein said first housing is spring biased toward said second housing.

18. The apparatus according to claim 17 wherein:

said rotatable housing includes a shaft having a gear mounted at the end of the shaft responsive to rotation force for causing rotation of the rotatable housing;

the shaft includes a snap fit member for receiving the gear and engaging the gear to retain the gear in a predetermined position on the shaft; and the snap fit feature is located opposite a load-bearing portion of the shaft.

19. The apparatus of claim 11 wherein said rotatable housing comprises a hook-shaped portion configured to engage the conduit and move the conduit to a position between the first and second housings during rotation of said one housing towards the other housing thereby capturing and aligning the conduit.

20. The apparatus of claim 11 wherein said rotatable housing comprises an arcuate tapered flare configured to engage the conduit and to wipe the exterior of the conduit during rotation of said one housing towards the other housing to thereby clean the conduit of matter located on its exterior.

21. The apparatus of claim 11 further comprising a guide member located adjacent one of said housings to contain the conduit within a predetermined range of the rotatable housing.

22. The apparatus of claim 21 wherein said guide member has approximately a half-dome shape and extends to a height approximately equal to the height of the rotatable housing.

23. An apparatus for detecting gas in a fluid conduit, comprising:

a first housing fixedly mounted to a base and having a first arcuate section for matingly contacting a first arcuate section of said conduit;

a second housing pivotally mounted to said base, said second housing being rotatable relative to said first housing, said second housing having a second arcuate section, said second housing being rotatable so that said second arcuate section of said second housing matingly contacts a second arcuate section of said conduit;

a first transducer mounted in one of said housings for transmitting a signal across said conduit; and a second transducer associated in the other of said second housings for receiving said transmitted signal;

whereby said signal travels across said conduit and is received by said second transducer which converts said signal into an electrical signal which is processed and which will establish whether said conduit is carrying the liquid or the gas.

24. The apparatus according to claim 23, wherein when said second housing is rotated, said first housing and said second housing are spaced a predetermined distance apart.

25. The apparatus according to claim 24, wherein said first housing is spring biased toward said second housing to set said predetermined spaced apart distance so that when said second housing is rotated into contact with said conduit, said conduit opposes said spring bias to move said first housing away from said second housing a distance greater than said predetermined distance.

26. The apparatus according to claim 23, wherein when said second housing is rotated, said conduit is compressed between said first arcuate section of said first housing and said second arcuate section of said second housing.

27. The apparatus according to claim 23, wherein said signal from said first transducer is an ultrasonic signal which passes through said conduit and through the liquid or the gas in said conduit.

28. The apparatus according to claim 23, wherein said first arcuate section is aligned substantially parallel to said second arcuate section when said second housing is rotated.

29. The apparatus according to claim 28, wherein said second arcuate section further comprises an arcuate tapered flare to slidably engage said conduit when said second housing is rotated for aligning said conduit between said substantially parallel first and second arcuate sections.

30. The apparatus according to claim 23, wherein said first arcuate section of said first housing comprises a concave arc of approximately 90 degrees.

31. The apparatus according to claim 23, wherein said second arcuate section of said second housing comprises a concave arc of approximately 90 degrees.

32. The apparatus of claim 23 wherein said second housing comprises a hook-shaped portion formed on the rotatable housing, the hook-shaped portion configured to engage the conduit and move the conduit to a position between the first and second housings during rotation of said one housing towards the other housing thereby capturing and aligning the conduit.

33. The apparatus of claim 23 wherein said means for capturing and aligning comprises a guide member located adjacent one of said housings to contain the conduit within a predetermined range of the rotatable housing.

34. The apparatus of claim 33 wherein said guide member has approximately a half-dome shape and extends to a height approximately equal to the height of the rotatable housing.

35. An apparatus for detecting a gas in a liquid contained in a conduit, comprising:

a first housing having a first surface with a first fillet formed therein;

a first transducer affixed to said first housing adjacent said first fillet;

a second housing, having a second surface with a second fillet formed therein, wherein said second housing is shiftable relative said first housing and is configured such that at least a portion of said second fillet becomes positioned adjacent and parallel to said first fillet upon shifting said second housing such that said second housing slidingly engages said conduit to align and capture said conduit between said first and second fillets; and a second transducer affixed to said second housing, adjacent said second fillet.

36. The apparatus of claim 35 wherein said second fillet is formed to flare upwardly and laterally away from said first fillet upon positioning of said second housing such that said portion of second fillet is adjacent and parallel to said first fillet.

37. The apparatus of claim 36 wherein one of said housings is biased toward the other.

38. The apparatus of claim 36 wherein said second housing comprises a hook-shaped portion configured to engage the tubing and move the tubing to a position between the first and second housings during shifting of said second housing towards the first housing thereby capturing and aligning the tubing.

39. The apparatus of claim 38 wherein said second housing comprises an arcuate tapered flare configured to engage the tubing and to wipe the exterior of the tubing during shifting of said second housing towards the first housing to thereby clean the tubing of matter located on its exterior.

40. The apparatus of claim 39 further comprising a guide member located adjacent said first housing to contain the tubing within a predetermined range of the second housing.

41. The apparatus of claim 40 wherein said guide member has approximately a half-dome shape and extends to a height approximately equal to the height of the second housing.

* * * * *